United States Patent [19]

Sauter et al.

[11] 4,380,546
[45] Apr. 19, 1983

[54] AZOLE COMPOUNDS, THEIR PREPARATION, THEIR USE FOR CROP TREATMENT, AND AGENTS FOR THIS PURPOSE

[75] Inventors: Hubert Sauter, Mannheim; Eberhard Ammermann, Ludwigshafen; Costin Rentzea, Heidelberg; Bernd Zeeh, Ludwigshafen; Johann Jung; Ernst-Heinrich Pommer, both of Limburgerhof, all of Fed. Rep. of Germany

[73] Assignee: BASF Aktiengesellschaft, Fed. Rep. of Germany

[21] Appl. No.: 258,789

[22] Filed: Apr. 29, 1981

[30] Foreign Application Priority Data

May 19, 1980 [DE] Fed. Rep. of Germany ....... 3019049

[51] Int. Cl.³ .................... A01N 43/50; A01N 43/64; C07D 233/60; C07D 249/08
[52] U.S. Cl. ........................ 424/269; 71/74; 71/76; 71/78; 71/92; 424/245; 424/273 R; 548/101; 548/262; 548/341; 568/642; 568/648; 568/649; 568/655; 568/656
[58] Field of Search .............. 548/101, 341, 262; 424/269, 273 R, 245; 71/76, 92, 74, 76

[56] References Cited

U.S. PATENT DOCUMENTS

| 4,005,083 | 1/1977 | Büchel et al. | 424/245 |
|---|---|---|---|
| 4,145,428 | 3/1979 | Krämer et al. | 548/262 |
| 4,217,129 | 8/1980 | Shephard et al. | 548/262 |
| 4,229,459 | 10/1980 | Krämer et al. | 424/232 |
| 4,316,932 | 2/1982 | Kranz et al. | 424/269 |

FOREIGN PATENT DOCUMENTS

| 340410 | 4/1977 | Austria | 548/341 |
|---|---|---|---|
| 2063857 | 7/1971 | Fed. Rep. of Germany | 548/262 |
| 2431073 | 1/1976 | Fed. Rep. of Germany | 548/262 |
| 2638470 | 3/1977 | Fed. Rep. of Germany | 548/262 |
| 2739352 | 3/1979 | Fed. Rep. of Germany | 548/262 |
| 2838847 | 3/1979 | Fed. Rep. of Germany | 548/341 |
| 2800544 | 7/1979 | Fed. Rep. of Germany | 548/262 |
| 2842137 | 4/1980 | Fed. Rep. of Germany | 548/262 |

OTHER PUBLICATIONS

J. Biological Chemistry 235 (1960), pp. 475-479.

*Primary Examiner*—Alton D. Rollins
*Attorney, Agent, or Firm*—Keil & Witherspoon

[57] ABSTRACT

Azole compounds of the formula

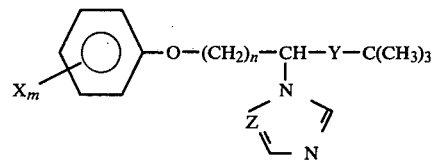

where X is hydrogen, halogen, $C_1$-$C_4$-alkyl, $C_1$-$C_4$-alkoxy, trifluoromethyl or phenyl and m is an integer from 1 to 5, and, if m is greater than 1, the X's can be identical or different, n is an integer from 2 to 5, Z is N or CH and Y is CO or $CR^1OR^2$, where $R^1$ is hydrogen or $C_1$-$C_4$-alkyl and $R^2$ is hydrogen, $C_1$-$C_4$-alkyl, $C_2$-$C_4$-alkenyl, $C_2$-$C_4$-alkynyl or $C_1$-$C_4$-alkanoyl, and their crop-tolerated addition salts with acids, and metal complexes.

The compounds act as fungicides and growth regulators.

9 Claims, No Drawings

AZOLE COMPOUNDS, THEIR PREPARATION, THEIR USE FOR CROP TREATMENT, AND AGENTS FOR THIS PURPOSE

The present invention relates to novel, valuable azole compounds, processes for their preparation, crop treatment agents containing the novel compounds, and the use of these agents.

The good fungicidal activity of imidazole derivatives, for example 1-(2,4-dichlorophenyl β-allyl-ethyl ether)-imidazole (German Laid-Open Application DE-OS No. 2,063,857) and of triazole derivatives, for example 2,2-dimethyl-4-(1,2,4-triazol-1-yl)-5-phenyl-pentan-3-one (German Laid-Open Application DE-OS No. 2,638,470) has been disclosed. However, when low amounts and low concentrations are used, the effect is not always satisfactory. Furthermore, the fungitoxic action is often associated with high phytotoxicity, so that at the concentrations required for control of fungi in crop protection, for example for the control of rust fungi, the crop plants are also damaged. For these reasons, the compounds are not always suitable for use as crop protection agents for controlling fungi, nor are they suitable for use with all types of crops.

Further, it has been disclosed that quaternary ammonium compounds, such as chlorocholine chloride (CCC) (J. Biol. Chem. 235 (1960), 475), and certain triazole derivatives, for example 3-(1,2,4-triazol-1-yl)-1-(4-chlorophenyl)-4,4-dimethylpentan-1-one (German Laid-Open Application DE-OS No. 2,739,352) have an effect on the growth of crop plants and can be used as plant growth regulators. However, the plant growth-regulating action is not always satisfactory, especially when low amounts are used.

We have found novel compounds which exhibit a very high fungitoxic action coupled with excellent toleration by crops. The novel compounds furthermore show powerful plant growth-regulating effects, coupled with very good toleration by crops, even when used in low amounts.

The present invention relates to novel azole compounds of the formula I

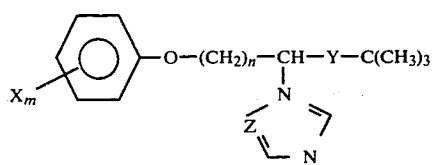

(I)

where X is hydrogen, halogen, $C_1$-$C_4$-alkyl, $C_1$-$C_4$-alkoxy, trifluoromethyl or phenyl and m is an integer from 1 to 5, and, if m is greater than 1, the X's can be identical or different, n is an integer from 2 to 5, Z is N or CH and Y is CO or $CR^1OR^2$, where $R^1$ is hydrogen or $C_1$-$C_4$-alkyl and $R^2$ is hydrogen, $C_1$-$C_4$-alkyl, $C_2$-$C_4$-alkenyl, $C_2$-$C_4$-alkynyl or $C_1$-$C_4$-alkanoyl, as well as their addition salts with acids and their metal complex salts.

In the novel compounds of the formula I, the azolyl-substituted carbon atom is a chiral atom; accordingly, the products are obtained as enantiomer mixtures, which can be separated into the optically active compounds. In the case of the alcohols, ethers or esters ($Y=CR^1OR^2$), the additional chiral center results in diastereomer mixtures which can be separated into the individual components in a conventional manner, for example by crystallization or chromatography. However, if the novel compounds are to be used as fungicides or plant growth regulators, separation of the enantiomers or diastereomers is normally not necessary.

Examples of possible meanings of $X_m$ on the phenoxy radical are hydrogen, 2-fluoro-, 4-fluoro-, 2-chloro-, 3-chloro-, 4-chloro-, 4-bromo-, 2,4-dichloro-, 2,4,6-trichloro-, 3,5-dichloro-, 2-chloro-4-phenyl-, 2-methyl-4-chloro-, 2-methyl-, 3-methyl-, 4-methyl-, 3-tert.-butyl-, 4-tert.-butyl-, 2-methoxy-, 3-methoxy-, 4-methoxy-, 3,5-dimethoxy-, 3-n-butoxy-, 4-n-butoxy-, 2-methoxy-4-methyl- and 3-trifluoromethyl-.

$R^1$ is, for example, hydrogen, methyl, ethyl, n-propyl, isopropyl or n-butyl.

$R^2$ is, for example, hydrogen, methyl, ethyl, n-propyl, prop-2-en-1-yl, prop-2-yn-1-yl, n-butyl, 2-methylprop-2-en-1-yl, acetyl, propionyl, butyryl or isobutyryl.

Examples of suitable addition salts are salts with hydrobromic acid, sulfuric acid, nitric acid, phosphoric acid, oxalic acid or dodecylbenzenesulfonic acid. As the activity of the salts is attributable to the cation, any anion may be selected.

Suitable metal complexes are compounds of the formula

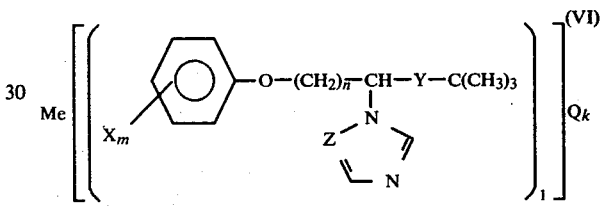

(VI)

where $X_m$, n, Z and Y have the above meanings and Me is a metal, for example copper, zinc, tin, manganese, iron, cobalt or nickel, Q is the anion of an inorganic acid, for example hydrochloric acid, sulfuric acid, phosphoric acid or hydrobromic acid and l and k are 1, 2, 3 or 4.

The invention further relates to a process for the preparation of the azole compounds of the formula I as claimed in claim 1, wherein a ketone of the formula II

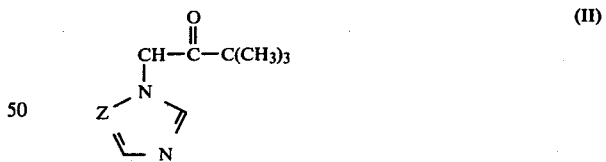

(II)

where Z has the above meanings, or an alkali metal enolate thereof, is reacted with a ω-aryloxyalkyl halide of the formula III

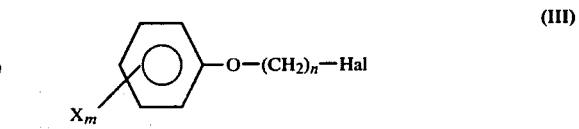

(III)

where X, m and n have the meanings given in claim 1 and Hal is chlorine, bromine or iodine, in the presence or absence of a solvent or diluent and/or of an inorganic or organic base, at from 0° to 100° C., after which the resulting compound of the formula I, where Y is a CO group, can, if desired, be reduced to form the corresponding alcohol, by treatment with a complex hydride or by treatment with hydrogen in the presence of a hydrogenation catalyst, in the presence or absence of a solvent or diluent, at from 0° to 100° C., to a secondary alcohol of the formula I, where Y is a CHOH group, or be reacted with a Grignard compound of the formula IV $R^1$—MgHal    IV where $R^1$ is $C_1$-$C_4$-alkyl and Hal is chlorine, bromine or iodine, in the presence or absence of a solvent or diluent and in the presence or absence of a magnesium halide or tetraalkylammonium halide, at from 0° to 100° C., the resulting alcoholate then being hydrolyzed to the tertiary alcohol. The secondary or tertiary alcohol thus obtained can, if desired, be reacted with a $C_1$-$C_4$-alkanoyl chloride or a $C_1$-$C_4$-alkanoyl anhydride to form the corresponding ester, in the presence or absence of a solvent or diluent and/or of an inorganic or organic base and/or of an acylation catalyst, at from 0° to 100° C. Alternatively, they or their alkali metal salts or their quaternary ammonium salts can, for the preparation of the corresponding ethers, be reacted with an alkylating agent of the formula V

L—$R^2$    V, where $R^2$ is $C_1$-$C_4$-alkyl, $C_2$-$C_4$-alkenyl or $C_2$-$C_4$-alkynyl and L is a nucleophilically displaceable leaving group, in the presence or absence of a solvent or diluent and/or of an inorganic or organic base and/or of a reaction accelerator, at from 0° to 100° C. The various compounds of the formula I which are thus obtained can, if desired, subsequently be converted to their crop-tolerated addition salts with acids, or metal complexes.

In the process for the preparation of a ketone of the formula I, where R is a CO group, a known ketone of the formula II (German Laid-Open Application DOS No. 2,638,470) or an alkali metal enolate thereof is alkylated with a ω-aryloxyalkyl halide III, in the presence or absence of a base and/or of a solvent or diluent, to give the novel ketone of the formula Ia.

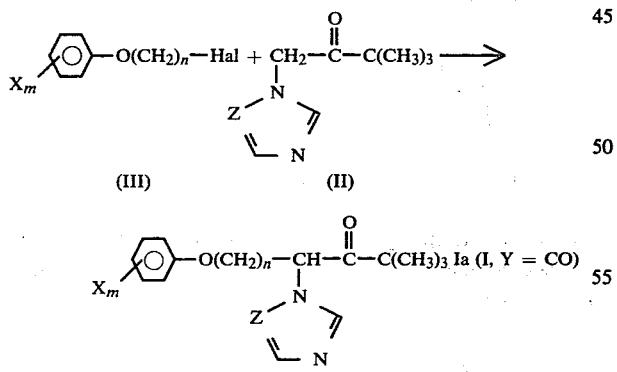

To carry out this reaction, the ketone II can first be metallized to give the alkali metal enolate, by reacting it, preferably in the presence of a polar aprotic solvent such as dimethylformamide, acetonitrile or tetrahydrofuran, with 0.8–1.2 equivalents, preferably 1.0 equivalent, of a metallizing agent, such as sodium hydride, lithium diisopropylamide or n-butyl-lithium, at 0°–100° C., preferably at 10°–50° C. On subsequent addition of 0.8–2.0, preferably 1.0, equivalent of the particular ω-aryloxyalkyl halide of the formula III, at 0°–100° C., preferably at 5°–30° C., the ketone of the formula I is obtained.

In another embodiment of this process, the ketone II is reacted with the ω-aryloxyalkyl halide III in the presence of 0.8–1.2 equivalents, preferably 1.0 equivalent, of a base, for example potassium tert.-butoxide, sodium methoxide or potassium hydroxide, the reaction advantageously being carried out in the presence of a solvent or diluent, at 0°–100° C., preferably at 5°–50° C.

Suitable solvents or diluents are, once again, dipolar aprotic solvents, but alcohols, such as methanol or tert.-butanol, can also be used.

The ω-aryloxyalkyl halides III are known compounds or can easily be prepared by conventional methods, for example by monoalkylating a phenol with an aliphatic dihaloalkane, eg. with 1,2-dibromoethane, 1,3-dichloropropane, 1,4-dibromobutane or 1,5-dibromopentane (cf. Houben-Weyl, Methoden der Organischen Chemie, Volume 6/3, pages 54–59, Thieme-Verlag, Stuttgart, 1965, and Examples 1b and 5).

In the process for the preparation of the secondary alcohols of the formula I, in which Y is the group $$-\overset{OH}{\underset{H}{C}}-,$$

a ketone of the formula I, in which R is a CO group, is reduced, for example by treatment with a complex hydride, preferably sodium borohydride, in the presence of a polar solvent, for example an alcohol, preferably methanol or ethanol, at from 0° to 100° C., and the product is then hydrolyzed with an aqueous base or acid; alternatively, the ketone of the formula I is treated with hydrogen in the presence of a hydrogenation catalyst, such as platinum or Raney nickel, and of a polar solvent, such as methanol, ethanol or ethyl acetate, at from 20° to 100° C. and at a pressure of from 1 to 100 bar:

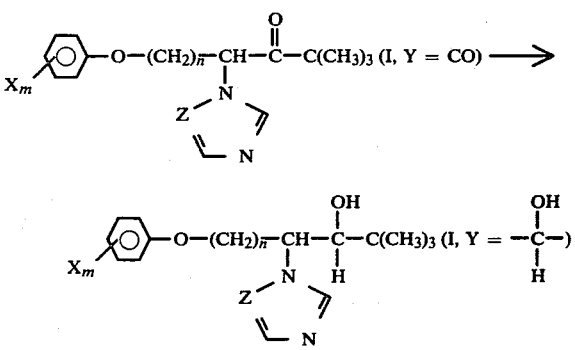

In the process for the preparation of the tertiary alcohols of the formula I $$(Y = -\overset{OH}{\underset{R^1}{C}}-,$$

where $R^1$ is $C_1$-$C_4$-alkyl, but is not hydrogen), a ketone of the formula I (Y=CO) is reacted with 0.8–1.2 equivalents of a Grignard compound of the formula IV $$R^1\text{—MgHal} \qquad \text{IV}$$

where $R^1$ is $C_1$-$C_4$-alkyl and Hal is chlorine, bromine or iodine, preferably in the absence of a solvent and in the presence or absence of a salt which increases the yield:

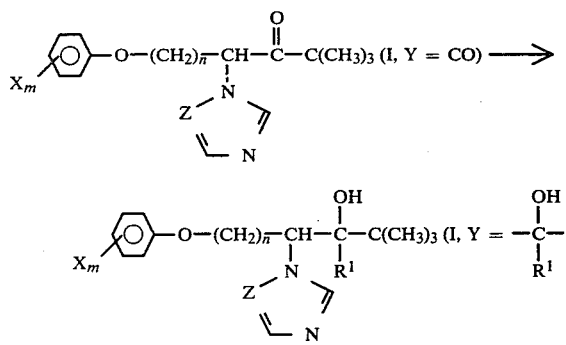

If a solvent is used, it is preferably an ether, such as diethyl ether, di-n-propyl ether, tetrahydrofuran or anisole, or a tertiary amine, such as N,N-diethylaniline, or hexamethylphosphoramide; at times, the reaction can also be carried out in a mixture of these solvents with aliphatic or aromatic hydrocarbons, such as n-hexane or toluene. Salts which increase the yield and which suppress the usual side-reactions are, in particular, anhydrous magnesium halides, such as anhydrous magnesium bromide, or anhydrous tetraalkylammonium halides, for example tetra-n-butylammonium chloride. The reaction temperature can be from 0° to 100° C., depending on the solvent, but is preferably from 0° to 60° C. The magnesium alcoholate first formed in the reaction is then converted to the alcohol by hydrolysis with a dilute aqueous acid, such as hydrochloric acid, sulfuric acid or, preferably, acetic acid, or, as a particularly preferred method, with aqueous ammonium chloride solution; after removal of the aqueous phase, the alcohol can, if desired, be purified in a conventional manner by extraction, recrystallization or chromatography.

In the process for the preparation of the esters of the formula I

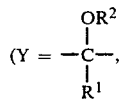

where $R^2$ is acetyl, propionyl, n-butyryl or isobutyryl), the secondary or tertiary alcohol of the formula I

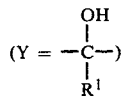

is reacted with the corresponding acid chloride or acid anhydride, in the presence of an acid acceptor and in the presence or absence of an aprotic solvent or diluent, and preferably in the presence of an acylation catalyst, at from 0° to 100° C., preferably from 10° to 50° C. The acid acceptor, employed in not less than the equivalent amount, can be an inorganic base, such as sodium amide or, particularly preferentially, pyridine. The acylation catalyst used is advantageously imidazole or 4-dimethylaminopyridine, in an amount of 0.01–0.4 equivalent, unless pyridine is in any case present. The solvent employed can be a hydrocarbon, eg. cyclohexane or toluene, an ether, eg. diethyl ether, tetrahydrofuran or dioxane, a ketone, eg. acetone or diethyl ketone, or an excess of an acid-accepting amine, eg. triethylamine or pyridine.

In the process for the preparation of the ethers of the formula I

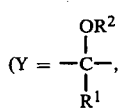

where $R^2$ is $C_1$-$C_4$-alkyl, $C_2$-$C_4$-alkenyl or $C_2$-$C_4$-alkynyl), a secondary or tertiary alcohol of the formula I

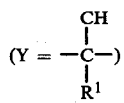

or an alkali metal salt or quaternary ammonium salt thereof, is reacted with an alkylating agent of the formula V $$L\text{—}R^2 \qquad V$$

at from 0° to 100° C., in the presence or absence of a solvent or diluent, and in the presence or absence of an inorganic or organic base and/or of a reaction accelerator.

Examples of the nucleophilically displaceable leaving groups L referred to above are halogen, preferably chlorine, bromine or iodine, an alkyl-sulfate group, preferably methyl-sulfate, a substituted or unsubstituted alkylsulfonyloxy radical, preferably methanesulfonyloxy or trifluoromethanesulfonyloxy, and an arylsulfonyloxy radical, preferably a tosylate.

Examples of suitable inorganic or organic bases, which can, where appropriate, also be employed as acid acceptors in the reaction, are alkali metal hydroxides and alkaline earth metal hydroxides, such as sodium hydroxide, potassium hydroxide and calcium hydroxide, alkali metal carbonates, such as potassium carbonate and sodium carbonate, alkali metal hydrides, such as sodium hydride, alkali metal alcoholates and alkaline earth metal alcoholates, such as sodium methylate, magnesium methylate and sodium isopropylate, and tertiary amines, such as trimethylamine, triethylamine, N,N-dimethylaniline, N,N-dimethylcyclohexylamine, N-methylpiperidine and pyridine. However, other conventional bases can also be used.

It is also possible, using a suitable base, for example an alkali metal hydride, such as sodium hydride, or a lithium alkyl, such as butyl-lithium, or an alkali metal alcoholate or alkaline earth metal alcoholate, such as sodium methylate, first to convert the alcohol of the formula II, in a preliminary reaction, to its alcoholate salt, and then carry out the reaction with this product.

The preferred solvents and diluents include halohydrocarbons, eg. methylene chloride, chloroform, 1,2-dichloroethane and chlorobenzene, aliphatic and aromatic hydrocarbons, eg. cyclohexane, petroleum ether, benzene, toluene and xylenes, esters, eg. ethyl acetate, amides, eg. dimethylformamide, nitriles, eg. acetonitrile, sulfoxides, eg. dimethylsulfoxide, ketones, eg. acetone and methyl ethyl ketone, ethers, eg. diethyl ether, tetrahydrofuran or dioxane, or mixtures of the above.

Preferred reaction accelerators are metal halides, eg. potassium iodide, crown ethers, quaternary ammonium compounds, eg. tetrabutylammonium iodide, and acids, as well as combinations of these accelerators.

The reactions according to the invention are in general carried out at from 0° to 100° C., for from 1 to 60 hours, continuously or batchwise, under atmospheric or superatmospheric pressure.

The conventional methods are followed in order to isolate the novel compounds. In general, the products as obtained do not require additional purification, but they can be purified further by conventional methods, such as recrystallization, extraction, distillation or chromatography.

Where desired, a novel compound of the formula I can also be converted to a salt with an inorganic or organic acid, for example to a salt with hydrochloric acid, hydrobromic acid, nitric acid, oxalic acid, acetic acid, sulfuric acid, phosphoric acid or dodecylbenzenesulfonic acid. As the activity of the salts is attributable to the cation, any anion may be selected.

A compound of the formula I can also be converted to metal complexes by conventional methods, for example by reacting the compound with a suitable metal salt, eg. copper(II) chloride, zinc(II) chloride, iron(III) chloride, copper(II) nitrate, manganese(II) chloride and nickel(II) bromide.

The Examples which follow illustrate the preparation of the novel compounds of the formula I:

EXAMPLE 1

(a) Preparation of the intermediate 1-bromo-4-phenoxybutane

A mixture of 329 g of phenol, 484 g of dry potassium carbonate, 756 g of 1,4-dibromobutane and 1,000 ml of cyclopentanone is refluxed for 24 hours, whilst stirring. The solid constituents are filtered off and the filtrate is then concentrated under reduced pressure; the oily residue is taken up in 1,500 ml of methylene chloride and this solution is extracted ten times with 200 ml of 15 percent strength aqueous sodium hydroxide solution at a time. The organic phase is then extracted twice with 300 ml of water at a time, dried over magnesium sulate, filtered and concentrated under reduced pressure. Distillation of the residue gives, at 92°–98° C./0.4 mbar, 395 g of colorless 1-bromo-3-phenoxybutane, which solidifies in the receiver; melting point 33°–36° C.

(b) Preparation of the end product 2,2-dimethyl-4-(1,2,4-triazol-1-yl)-8-phenoxy-octan-3-one A solution of 14.3 g of 2,2-dimethyl-4-(1,2,4-triazol-1-yl)-butan-3-one (cf. German Laid-Open Application DOS No. 2,638,470) in 20 ml of DMF is added dropwise, under a dry nitrogen atmosphere, to a stirred suspension of 2.3 g of sodium hydride in 20 ml of dimethylformamide (DMF), the reaction temperature being kept at 20°–30° C. by cooling; the mixture is subsequently stirred for 20 hours at room temperature. A solution of 19.5 g of 1-bromo-4-phenoxybutane in 20 ml of DMF is then added dropwise at 5°–10° C., with continued stirring, and whilst cooling with ice. After completion of the addition, stirring is continued for 10 hours at 5°–10° C., after which 200 ml of water are added and the mixture is extracted twice with 100 ml of methylene chloride at a time. The combined organic phases are extracted by shaking with water and dried over magnesium sulfate; removal of the solvent under reduced pressure gives an oil from which, on trituration with 20 ml of diisopropyl ether, 17 g of colorless crystals precipitate; melting point 59°–62° C.

EXAMPLE 2

2,2-Dimethyl-4-(1,2,4-triazol-1-yl)-8-phenoxy-octan-3-ol 72 g of solid sodium borohydried are added, a little at a time, to a stirred solution of 600 g of 2,3-dimethyl-4-(1,2,4-triazol-1-yl)-8-phenoxy-octan-3-ol in 1,000 ml of methanol; during the addition, the mixture reaches the refluxing temperature. When the exothermic reaction has subsided, the mixture is evaporated to dryness under reduced pressure. 500 ml of water are added to the residue and the batch is extracted three times with 300 ml of methylene chloride at a time. The combined organic phases are dried over magnesium sulfate and filtered, and the filtrate is concentrated under reduced pressure. 200 ml of diisopropyl ether are added to the residue, and 360 g of colorless crystals, of melting point 79°–81° C., are isolated from this mixture.

EXAMPLE 3

2,2-Dimethyl-3-methoxy-4-(1,2,4-triazol-1-yl)-8-phenoxyoctane

A solution of 15.4 g of 2,2-dimethyl-4-(1,2,4-triazol-1-yl)-8-phenoxy-octan-3-ol in 50 ml of DMF is added dropwise to a suspension of 1.6 g of sodium hydride in 50 ml of DMF. The mixture is then stirred for 2 hours under reflux. When it has cooled to room temperature, 3.7 ml of methyl iodide are added. This mixture is stirred for five hours under reflux, 200 ml of water are then added, the reaction mixture is extracted three times with 100 ml of diethyl ether at a time and the combined extracts are washed three times with 50 ml of water at a time, dried over magnesium sulfate and concentrated under reduced pressure. The residue consists of 2.2 g of a yellowish resin. Infrared spectrum (film): 2,930, 2,862, 1,588, 1,576, 1,486, 1,460 1,264, 1,233, 1,126, 1,080, 1,005, 745, 682 and 670 cm$^{-1}$.

EXAMPLE 4

2,2-Dimethyl-3-acetoxy-4-(1,2,4-triazol-1-yl)-phenoxyoctane

A mixture of 10 g of 2,2-dimethyl-4-(1,2,4-triazol-1-yl)-8-phenoxy-octan-3-ol, 20 ml of acetic anhydride and 1 g of imidazole is refluxed for 18 hours. When the mixture has cooled to room temperature, it is taken up in 150 ml of methylene chloride and is extracted by shaking five times with 50 ml of water at a time, five times with 50 ml of saturated aqueous sodium carbonate solution at a time, and finally once more with water. On concentrating the organic phase under reduced pressure, 7.9 g of a brownish resin are obtained. Infrared spectrum (film): 2,938, 2,860, 1,730, 1,588, 1,576, 1,487, 1,462, 1,361, 1,264, 1,225, 1,162, 1,128, 1,011, 745, 682 and 671 cm$^{-1}$.

EXAMPLE 5

2,2-Dimethyl-4-(1,2,4-triazol-1-yl)-6-phenoxy-hexan-3-one 2.6 g of sodium hydride, 16.7 g of 2,2-dimethyl-4-(1,2,4-triazol-1-yl)-butan-3-one and 20.1 g of 1-bromo-2-phenoxyethane are reacted by a method similar to that of Example 1b.

11.4 g of product are obtained; melting point 37°–40° C.

EXAMPLE 6

2,2,3-Trimethyl-4-(1,2,4-triazol-1-yl)-6-phenoxy-hexan-3-ol

A solution of 6.0 g of 2,2-dimethyl-4-(1,2,4-triazol-1-yl)-6-phenoxy-hexan-3-one in 50 ml of tetrahydrofuran is added dropwise to a solution of 5.4 g of methyl-magnesium bromide in 28 ml of tetrahydrofuran, and after the slight exothermic reaction has subsided the mixture is left to stand for 24 hours at room temperature. It is then poured into 1,000 ml of 10% strength aqueous ammonium chloride solution and the batch is extracted twice with 200 ml of methylene chloride at a time. The organic phase is washed and dried over magnesium sulfate, and the methylene chloride is evaporated off under reduced pressure. 10 ml of diisopropyl ether are added to the residue, and 1.5 g of white crystals, of melting point 118°–120° C., are isolated from this mixture.

Further Examples of the compounds according to the invention, of the formula (I), are to be found in Table 1 below.

TABLE 1

| Ex. no. | $X_m$ | n | Z | Y | M.p. (°C.) |
|---|---|---|---|---|---|
| 7 | H | 4 | CH | CO | resin |
| 8 | H | 4 | CH | CHOH | 87–89 |
| 9 | H | 2 | N | CHOH | 84–88 |
| 10 | H | 2 | N | C(n-C$_3$H$_7$)OH | |
| 11 | 4-Cl | 2 | N | CO | 62–66 |
| 12 | 4-Cl | 2 | N | CHOH | 96–100 |
| 13 | 2,4-Cl$_2$ | 2 | N | CO | 56–58 |
| 14 | 2,4-Cl$_2$ | 2 | N | CHOH | 101–105 |
| 15 | H | 3 | N | CO | 55–58 |
| 16 | H | 3 | N | CHOH | 79–82 |
| 17 | 4-Cl | 3 | N | CO | 59–60 |
| 18 | 4-Cl | 3 | N | CHOH | 121–126 |
| 19 | 4-Cl | 4 | N | CO | 37–38 |
| 20 | 4-Cl | 4 | N | CHOH | 76–78 |
| 21 | 3-CF$_3$ | 2 | N | CO | 36–37 |
| 22 | 3-CF$_3$ | 2 | N | CHOH | 89–92 |
| 23 | 2-Cl, 4-Phenyl | 2 | N | CO | 109–113 |
| 24 | 2-Cl, 4-Phenyl | 2 | N | CHOH | 105–107 |
| 25 | 3-CH$_3$ | 2 | N | CO | 46–48 |
| 26 | 3-CH$_3$ | 2 | N | CHOH | 104–107 |
| 27 | H | 3 | N | C(CH$_3$)OH | 162–163 |
| 28 | 2-F | 2 | N | CO | resin |
| 29 | 2-F | 2 | N | CHOH | 83–87 |
| 30 | 4-F | 2 | N | CO | resin |
| 31 | 4-F | 2 | N | CHOH | 77–82 |
| 32 | 3-Cl | 2 | N | CO | 56–60 |
| 33 | 3-Cl | 2 | N | CHOH | 85–88 |
| 34 | 3-Cl | 3 | N | CO | resin |
| 35 | 3-Cl | 3 | N | CHOH | 74 |
| 36 | 2,4-Cl$_2$ | 3 | N | CO | 57 |
| 37 | 2,4-Cl$_2$ | 3 | N | CHOH | 82–84 |
| 38 | 2,4-Cl$_2$ | 4 | N | CO | 76–77 |
| 39 | 2,4-Cl$_2$ | 4 | N | CHOH | 91–93 |
| 40 | 3,5-Cl$_2$ | 2 | N | CO | 108–113 |
| 41 | 3,5-Cl$_2$ | 2 | N | CHOH | 80–84 |
| 42 | 3-CH$_3$ | 3 | N | CO | resin |
| 43 | 3-CH$_3$ | 3 | N | CHOH | 62 |
| 44 | 3-CF$_3$ | 3 | N | CO | resin |
| 45 | 3-CF$_3$ | 3 | N | CHOH | 65–69 |
| 46 | 2-OCH$_3$ | 2 | N | CO | resin |
| 47 | 2-OCH$_3$ | 2 | N | CHOH | resin |
| 48 | 3-OCH$_3$ | 2 | N | CO | 90–92 |
| 49 | 3-OCH$_3$ | 2 | N | CHOH | 101–104 |
| 50 | 4-OCH$_3$ | 2 | N | CO | 69–72 |
| 51 | 4-OCH$_3$ | 2 | N | CHOH | 92–94 |
| 52 | 4-OCH$_3$ | 3 | N | CO | 84–85 |
| 53 | 4-OCH$_3$ | 3 | N | CHOH | 104–108 |
| 54 | 3,5-(OCH$_3$)$_2$ | 2 | N | CO | 91–95 |
| 55 | 3,5-(OCH$_3$)$_2$ | 2 | N | CHOH | 104–105 |
| 56 | H | 4 | N | C(n-C$_3$H$_7$)OH | |
| 57 | H | 5 | N | CO | 61–63 |
| 58 | H | 5 | N | CHOH | 88–91 |
| 59 | 3-OCH$_3$ | 3 | N | CO | resin |
| 60 | 3-OCH$_3$ | 3 | N | CHOH | 69–72 |
| 61 | H | 4 | N | CHO-CH=CH$_2$ | resin |
| 62 | H | 4 | N | CHOH-CH=CH$_2$ | |
| 63 | H | 4 | N | C(n-C$_4$H$_9$)OH | |
| 64 | H | 4 | N | C(CH$_3$)OH | 114–117 |
| 65 | H | 5 | N | CHOCH$_3$ | resin |
| 66 | H | 5 | N | CHO-CH=CH$_2$ | resin |
| 67 | 2-OCH$_3$ | 3 | N | CO | |
| 68 | 2-OCH$_3$ | 3 | N | CHOH | 53–54 |
| 69 | 2-F | 3 | N | CO | |
| 70 | 2-F | 3 | N | CHOH | 76–77 |
| 71 | 3-F | 2 | N | CO | 55–56 |
| 72 | 3-F | 2 | N | CHOH | |
| 73 | 3-F | 3 | N | CO | 49–50 |
| 74 | 3-F | 3 | N | CHOH | 89–90 |
| 75 | 4-F | 3 | N | CO | |
| 76 | 4-F | 3 | N | CHOH | 110–112 |
| 77 | 4-F | 4 | N | CHOH | 86–88 |
| 78 | 4-F | 4 | N | C(CH$_3$)OH | 117–119 |
| 79 | H | 4 | CH | C(CH$_3$)OH | 66–69 |
| 80 | 4-Cl | 4 | N | C(CH$_3$)OH | 118–120 |
| 81 | 3-Cl | 4 | N | C(CH$_3$)OH | 90 |
| 82 | 3-CF$_3$ | 4 | N | C(CH$_3$)OH | 80 |

The compounds according to the invention, and the salts and metal complexes thereof, have an excellent action on a broad spectrum of fungi, especially plant-pathogenic fungi, particularly from the Ascomycetes and Basidiomycetes classes. Some of them have a systemic action and may be used as foliar and soil fungicides.

The fungicides according to the invention are of particular interest for combatting numerous fungi in various crop plants or their seed, particularly wheat, rye, barley, oats, rice, Indian corn, cotton, soybeans, coffee, sugarcane, fruit and ornamentals in horticulture, and vegetables such as beans, and cucumbers and other Cucurbitaceae.

The new compounds are especially suitable for combatting the following diseases: *Erysiphe graminis* in cereals, *Erysiphe cichoriacearum* in Cucurbitaceae, *Podosphaera leucotricha* in apples, *Uncinula necator* in grapes, *Erysiphe polygoni* in beans, *Sphaerotheca pannosa* in roses, *Puccinia* species in cereals, Rhizoctonia solani in cotton, Helminthosporium species in cereals, Ustilago species in cereals and sugarcane, Rhynchosporium secale in cereals and, especially, Venturia inaqeualis (apple scab).

Of the compounds of the formula I according to the invention, those are preferred as fungicides in which $X_m$ is H-, 4-Cl-, 2,4-Cl$_2$- or 3-CF$_3$-.

The compounds are applied by spraying or dusting the plants with the active ingredients or treating the seeds of the plants with the active ingredients. They may be applied before or after infection of the plants or seeds by the fungi.

The compounds of the invention can be converted into the conventional formulations, e.g. solutions, emulsions, suspensions, dusts, powders, pastes and granules. The form in which the compound is applied depends entirely on the end use but should in every case ensure fine uniform distribution of the active ingredient. The formulations are prepared in the conventional manner, for example by diluting the active ingredient with solvents and/or carriers, with or without the addition of emulsifiers and dispersants, and where water is used as the diluent, with or without an organic auxiliary solvent. Suitable auxiliaries are, essentially, solvents, for example aromatics, e.g. xylene and benzene, chloroaromatics, e.g. chlorobenzenes, paraffins, e.g. petroleum fractions, alcohols, e.g. methanol, and butanol, amines, e.g. ethanolamine and dimethylformamide, and water; carriers, for example natural rock powders, e.g. kaolin, alumina, talc and chalk, and synthetic rock powders, e.g. highly disperse silica and silicates; emulsifiers, for example non-ionic and anionic emulsifiers, e.g. polyoxyethylene fatty alcohol ethers, alkylsulfonates and arylsulfonates, and dispersants, for example lignin, sulfite waste liquors and methylcellulose.

The formulations in general contain from 0.1 to 95% by weight of active ingredient, preferably from 0.5 to 90%.

The amounts used depend on the nature of the desired effect, and range from 0.02 to 3 kg and more of active ingredient per hectare. The new compounds may also be used for the protection of materials, e.g., for combating wood-destroying fungi such as Coniophora puteana and Polystictus versicolor. The new active ingredients may further be used as fungicidally active components of oily wood preservatives for the protection of wood against wood-discoloring fungi. The wood is treated with these agents for instance by impregnation or coating.

The formulations, and the ready-to-use formulations obtained therefrom, e.g. solutions, emulsions, suspensions, powders, dusts, pastes or granules, are applied in the conventional manner, e.g. by spraying, atomizing, dusting, scattering, treating seed or watering.

Examples of such formulations are given below.

I. 90 parts by weight of the compound of Example 1 is mixed with 10 parts by weight of N-methyl-α-pyrrolidone. A mixture is obtained which is suitable for application in the form of very fine drops.

II. 20 parts by weight of the compound of Example 2 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene with 1 mole of castor oil. By pouring the solution into 100,000 parts by weight of water and uniformly distributing it therein, an aqueous dispersion is obtained containing 0.02% by weight of the active ingredient.

III. 20 parts by weight of the compound of Example 3 is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

IV. 20 parts by weight of the compound of Example 4 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

V. 20 parts by weight of the compound of Example 7 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of the compound of Example 2 is intimately mixed with 97 parts by weight of particulate kaolin. A dust is obtained containing 3% by weight of the active ingredient.

VII. 30 parts by weight of the compound of Example 1 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of the compound of Example 3 is intimately mixed with 10 parts of the sodium salt of a phenolsulfonic acid-urea-formaldehyde condensate, 2 parts of silica gel and 48 parts of water to give a stable, aqueous dispersion. Dilution in 100,000 parts by weight of water gives an aqueous dispersion containing 0.04 wt% of active ingredient.

IX. 20 parts of the compound of Example 4 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The above ready-to-use preparations may contain other active ingredients together with those according to the invention, e.g. herbicides, insecticides, growth regulators and other fungicides or may be mixed with fertilizers and applied together with these. When the active ingredients are mixed with other fungicides, the fungicidal spectrum of action is in many cases broadened.

The list of fungicides given below, with which the compounds according to the invention can be combined, is intended to illustrate the possible combinations, but the invention is in no way limited to these.

Examples of fungicides which can be combined with the compounds of the invention are: sulfur, dithiocarbamates and their derivatives, e.g. iron(III) dimethyldithiocarbamate, zinc dimethyldithiocarbamate, manganese N,N-ethylene-bis-dithiocarbamate, manganese zinc N,N-ethylenediamine-bis-dithiocarbamate, zinc N,N-ethylene-bis-dithiocarbamate, tetramethylthiuram disulfide, the ammonia complex of zinc N,N-ethylene-bis-dithiocarbamate and zinc N,N'-propylene-bis-dithiocarbamate, and the ammonia complex of zinc, N,N'-propylene-bis-dithiocarbamate and N,N'-polypropylene-bis-(thiocarbamoyl)-disulfide; nitro derivatives, e.g. dinitro-(1-methylheptyl)-phenyl crotonate, 2-sec.-butyl-4,6-dinitrophenyl-3,3-dimethylacrylate and 2-sec.-butyl-4,6-dinitrophenyl isopropyl carbonate; heterocyclic compounds, e.g. N-trichloromethylthiotetrahydrophthalimide, N-(1,1,2,2-tetrachloroethylthio)-tetrahydrophthalimide, N-trichloromethylthio-phthalimide, 2-heptadecyl-2-imidazoline acetate, 2,4-dichloro-6-(o-chloroanilino)-s-triazine, O,O-diethyl phthalimidophosphonothioate, 5-amino-1-(bis-(dimethylamino)-phosphinyl)-3-phenyl-1,2,4-triazole, 5-ethoxy-3-trichloromethyl-1,2,4-thiadiazole, 2,3-dicyano-1,4-dithiaanthraquinone, 2-thio-1,3-dithio-(4,5-b)-quinoxaline, methyl 1-(butylcarbamoyl)-2-benzimidazole-carbamate, 2-methoxycarbonylamino-benzimidazole, 2-thiocyanatomethylthio-benzthiazole, 4-(2-chlorophenylhydrazono)-3-methyl-5-isoxazolone, pyridine-2-thio-1-oxide, 8-hydroxyquinoline and its copper salt, 2,3-dihydro-5-carboxanilido-6-methyl-1,4-oxathiine-4,4-dioxide, 2,3-dihydro-5-carboxanilido-6-methyl-1,4-oxathiine, 2-fur-2-yl-benzimidazole, piperazine-1,4-diyl-bis-(1-(2,2,2-trichloroethyl)-formamide), 2-thiazol-4-yl-benzimidazole, 5-butyl-2-dimethylamino-4-hydroxy-6-methylpyrimidine, bis-(p-chlorophenyl)-3-pyridinemethanol, 1,2-bis-(3-ethoxycarbonyl-2-thioureido)-benzene, 1,2-bis-(3-methoxycarbonyl-2-thioureido)-benzene and various fungicides, e.g. dodecylguanidine acetate, 3-(2-(3,5-dimethyl-2-hydroxycyclohexyl)-2-hydroxyethyl)-glutarimide, hexachlorobenzene, N-dichlorofluoromethylthio-N',N'-dimethyl-N-phenyl-sulfuric acid diamide, 2,5-dimethyl-furan-3-carboxylic acid anilide, 2,5-dimethylfuran-3-carboxylic acid cyclohexylamide, 2-cyano-N-(ethylaminocarbonyl)-2-(methoxyimino)-acetamide, 2-methyl-benzoic acid anilide, 2-iodo-benzoic acid anilide, 1-(3,4-dichloroanilino)-1-formylamino-2,2,2-trichloroethane, 2,6-dimethyl-N-tridecyl-morpholine and its salts, 2,6-dimethyl-N-cyclodecyl-morpholine and its salts, DL-methyl-N-(2,6-dimethyl-phenyl)-N-fur-2-yl-alanate, methyl DL-N-(2,6-dimethyl-phenyl)-N-(2'-methoxyacetyl)-alanate, diisopropyl 5-nitroisophthalate, 1-(1',2',4'-triazol-1'-yl)-(4'-chlorophenoxy)-3,3-dimethyl-butan-2-one, 1-(1',2',4'-triazol-1'-yl)-(4'-chlorophenoxy)-3,3-dimethylbutan-2-ol, N-(2,6-dimethylphenyl)-N-chloroacetyl-D,L-2-aminobutyrolactone and N-(n-propyl)-N-(2,4,6-trichlorophenoxyethyl)-N'-imidazolylurea.

The biological action of the new compounds is demonstrated in Examples A and B below. The prior art compounds imazalil (1-(2'-(2'',4''-dichlorophenyl)-2'-(2''-propenyloxy)-ethyl)-1H-imidazole) and 2,2-dimethyl-4-(1,2,4-triazol-1-yl)-5-phenyl-pentan-3-one (German Laid-Open Application DE-OS No. 2,638,470) were used for comparison purposes.

EXAMPLE A

Action on wheat mildew

Leaves of pot-grown wheat seedlings of the "Jubilar" variety are sprayed with aqueous emulsions consisting of 80% (by weight) of active ingredient and 20% of emulsifier, and dusted after the sprayed-on layer has dried, with spores of wheat mildew (Erysiphe graminis var. tritici). The plants are then placed in a greenhouse at 20° to 22° C. and 75 to 80% relative humidity. The extent of mildew spread is determined after 10 days.

In this experiment, for example the compounds of Examples nos. 1, 2, 9, 11–13, 15–22, 24, 26, 29–34, 39, 41, 45, 47, 49 and 50 in particular had a better action than imazalil.

EXAMPLE B

Action on leaf rust of wheat

Leaves of pot-grown wheat seedlings of the "Caribo" variety are dusted with spores of leaf rust (Puccinia recondita). The pots are then placed in a high humidity (90–95%) chamber at from 20° to 22° C. for 24 hours. During this time, the spores germinate and the germ tubes penetrate into the leaf tissue. The infected plants are then sprayed to run-off with 0.025, 0.006 and 0.0015 wt% aqueous liquors, the solids comprising 80% of active ingredient and 20% of ligninsulfonate. After the spray coating has dried, the test plants are set up in a greenhouse at from 20° to 22° C. and from 65 to 70% relative humidity. After 8 days, the degree of development of the rust fungi on the leaves is determined.

In this experiment, for example the compounds of Examples nos. 2, 16–20, 22, 35, 43, 44 and 45 in particular had a better action than 2,2-dimethyl-4-(1,2,4-triazol-1-yl)-5-phenyl-pentan-3-one.

The new active ingredients according to the invention also influence plant metabolism, and may therefore be used as growth regulators.

Previous experience with growth regulators has shown that one active ingredient may have one or several different effects on plants.

The diversity of action of growth regulators depends especially on (a) the type and variety of plant;

(b) the time applied, with reference to the development stage of the plants and the time of year;

(c) the place and method of application (seed treatment, soil treatment, or application to leaves);

(d) geoclimatic factors (sunshine duration, average, temperature, precipitate);

(e) soil conditions (including fertilization);

(f) the formulation or application form of the active ingredient; and (g) the concentration at which the active ingredient is applied.

At all events, growth regulators are intended to influence crop plants in the desired manner.

A description of some of the various possibilities of using growth regulators in agriculture and horticulture is given below.

A. With the compounds according to the invention, vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, canal embankments and on areas such as parks, sportsgrounds, fruit orchards, lawns and airfields, thus reducing expensive and time-consuming mowing.

A further feature of economic interest is the increase in the rigor of crops which tend to lodge, such as cereals, Indian corn and soybeans. The shortening and strengthening of the stem thus caused reduces or eliminates the danger of lodging under unfavorable weather conditions.

The use of growth regulators is also important for inhibiting plant height and changing the time of ripening in cotton.

It is thus possible for this important crop to be harvested completely mechanically.

Growth regulators may also increase—or inhibit lateral branching. This is of interest when it is desired to inhibit, for instance in tobacco plants, the formation of lateral shoots (suckers) in favor of leaf development.

A further mechanism for increasing yields with growth regulators is based on the fact that blossom and fruit formation benefits to a greater extent from the nutrients when vegetative growth is restricted.

With growth regulators, it is possible for instance in winter rape to considerably increase the resistance to freeze injury. On the one hand, upward growth and the development of a too luxuriant (and thus particularly frost-susceptible) leaf or plant mass are inhibited; on the other, the young rape plants are kept, in spite of favorable growth conditions, in the vegetative development stage before winter frosts begin. The danger of freeze injury is thus eliminated in plants which tend to lose prematurely their inhibition to bloom and pass into the generative phase. In other crops, too, e.g., winter cereals, it is advantageous if the plants are well tillered in the fall as a result of treatment with the compounds according to the invention, but enter winter with not too lush a growth. This is a preventive measure against increased suspectibility to freeze injury and—because of the relatively low leaf or plant mass—attack by various diseases, especially fungus diseases. The inhibition of vegetative growth also makes closer planting possible in numerous crops, which means an increase in yield, based on the area cropped. The compounds according to the invention are particularly suitable for inhibiting vegetative growth in a broad spectrum of crop plants, such as wheat, rye, oats, Indian corn, sunflowers, groundnuts, tomatoes, various ornamentals, such as chysanthemums, poinsettias and hibiscus, cotton, and especially soybeans, rape, barley, rice and grasses.

B. Better yields both of plant parts and plant materials may be obtained with the active ingredients according to the invention. It is thus for instance possible to induce increased formation of buds, blossom, leaves, fruit, seed grains, roots and tubers, to increase the sugar content of sugar beets, sugarcane and citrus fruit, to raise the protein content of cereals and soybeans, and to stimulate the increased formation of latex in rubber trees.

The compounds according to the invention may raise the yield by influencing plant metabolism or by promoting or inhibiting vegetative and/or generative growth.

C. Finally, it is also possible with growth regulators to shorten or lengthen growth stages and to accelerate or retard the ripening process in plant parts either before or after harvesting.

A factor of economical interest is for example the facilitation of harvesting made possible by a chemical, temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also essential for a readily controllable defoliation of plants.

The compounds according to the invention may be applied to the crop either by treating the seed, treating the soil, i.e., through the roots, or—particularly preferred—by spraying the leaves. Because the active ingredients are well tolerated by the crop plants, application rates may vary within a wide range.

When the active ingredients are used to treat seed, active ingredient amounts of from 0.001 to 50 g, preferably from 0.01 to 10 g, per kg of seed are generally required.

When the active ingredients are applied to the soil or foliage, amounts of from 0.001 to 12 kg/ha, preferably from 0.01 to 3 kg/ha, are generally considered to be sufficient.

The compounds according to the invention may, when used as plant growth regulators, be converted into conventional formulations, as for fungicides above. The formulations thus obtained, or the ready-to-use preparations made therefrom, such as solutions, emulsions, suspensions, powders, dusts, pastes and granules, are applied in conventional manner, e.g., preemergence, postemergence or as seed dressings.

The growth-regulating agents according to the invention may, in these application forms, also be mixed and applied with other active ingredients, e.g., herbicides, insecticides, other growth regulators, bactericides, fungicides and fertilizers. When mixed with other growth regulators, the spectrum of action is in many cases increased; with a number of these compositions, synergistic effects also occur; i.e., the action of the combination product is greater than the effect of the individual components added together.

Of the compounds of the formula I according to the invention, those are preferred as growth regulators in which n is 2 or 3 (preferably 2), Z denotes N and Y denotes CO or CHOH.

To determine the growth-regulating properties of the compounds, test plants were grown in a soil provided with sufficient nutrients, in plastic pots 12.5 cm in diameter. In the preemergence treatment, the substances to be tested were sprayed, as aqueous formulations at various concentrations, onto the surface of the soil on the day the seeds were sown. In the postemergence treatment, the plants were sprayed with aqueous formulations at various concentrations. The growth-regulating action observed was confirmed at the end of the experiment by height measurement. The values obtained were compared with those for untreated plants. The comparative agents employed were 3-(1,2,4-triazol-1-yl)-1-(4-chlorophenyl)-4,4-dimethylpentan-1-one (German Laid-Open Application DE-OS 2,739,352) and (2-chloroethyl)-trimethylammonium chloride (CCC).

In these experiments, which were carried out on spring barley, rice, turf, spring rape and soybeans, for example the compounds of Examples nos. 1, 9, 12, 13, 14, 16, 17, 19, 22, 26, 27 and 29–35 in particular had a better action than the comparative agents.

We claim:

1. An azole compound of the formula

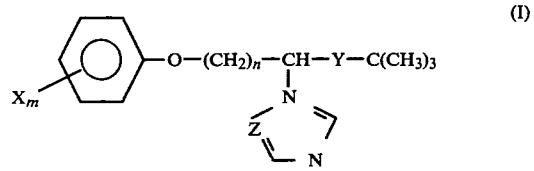

(I)

where X is hydrogen, halogen, $C_1$–$C_4$-alkyl, $C_1$–$C_4$-alkoxy, trifluoromethyl or phenyl and m is an integer from 1 to 5, and, if m is greater than 1, the X's can be identical or different, n is an integer from 2 to 5, Z is N or CH and Y is CO or $CR^1OR^2$, where $R^1$ is hydrogen or $C_1$–$C_4$-alkyl and $R^2$ is hydrogen, $C_1$–$C_4$-alkyl, $C_2$–$C_4$-alkenyl, $C_2$–$C_4$-alkynyl, as well as its addition salts with acids.

2. A plant treatment agent having fungicidal and growth regulating properties comprising a solid or liquid carrier and an effective amount of a compound of the formula I as described in claim 1.

3. A process for the prophylactic treatment of plants, wherein an effective amount of at least one compound of the formula I as described in claim 1 is allowed to act on plants, their seed, or the land on which they are grown.

4. A process for treating fungus diseases in plants which comprises: applying to the plants a fungicidally effective amount of a compound of the formula I as described in claim 1.

5. An azole compound of the formula (I) as defined in claim 1, which is 2,2-dimethyl-4-(1,2,4-triazol-1-yl)-8-phenoxy-octan-3-one.

6. An azole compound of the formula (I) as defined in claim 1, which is 2,2-dimethyl-4-(1,2,4-triazol-1-yl)-8-phenoxyoctan-3-ol.

7. An azole compound of the formula (I) as defined in claim 1, which is 2,2-dimethyl-4-(1,2,4-triazol-1-yl)-6-phenoxyhexan-3-ol.

8. An azole compound of the formula (I) as defined in claim 1, which is 2,2-dimethyl-4-(1,2,4-triazol-1-yl)-5-(4-fluorophenoxy)-hexan-3-ol.

9. An azole compound of the formula (I) as defined in claim 1, which is 2,2,3-trimethyl-4-(1,2,4-triazol-1-yl)-8-phenoxy-octan-3-ol.

* * * * *